(12) United States Patent
Abramson (10) Patent No.: US 7,819,122 B2
(45) Date of Patent: *Oct. 26, 2010

(54) MOUTH GUARD INCLUDING NASAL DILATOR FOR IMPROVED BREATHING

(76) Inventor: Mark E. Abramson, 6 Malory Ct., Redwood City, CA (US) 94061

( * ) Notice: Subject to any disclaimer, the term of this patent is extended or adjusted under 35 U.S.C. 154(b) by 0 days.

This patent is subject to a terminal disclaimer.

(21) Appl. No.: 12/508,468

(22) Filed: Jul. 23, 2009

(65) Prior Publication Data

US 2009/0301500 A1 Dec. 10, 2009

Related U.S. Application Data

(60) Continuation of application No. 11/485,942, filed on Jul. 13, 2006, now Pat. No. 7,581,542, which is a division of application No. 10/386,063, filed on Mar. 10, 2003, now Pat. No. 7,328,705.

(51) Int. Cl.
*A61C 5/14* (2006.01)
(52) U.S. Cl. .................................................. 128/848
(58) Field of Classification Search ................ 128/848, 128/859, 861, 862; 433/6; 602/902
See application file for complete search history.

(56) References Cited

U.S. PATENT DOCUMENTS

| | | | |
|---|---|---|---|
| 1,674,336 A | 6/1928 | King | |
| 2,685,287 A * | 8/1954 | Golfier et al. | 601/23 |
| 2,705,006 A | 3/1955 | Cettel | |
| 3,943,924 A | 3/1976 | Kallestad et al. | 128/136 |
| 4,044,762 A | 8/1977 | Jacobs | 128/136 |
| 4,063,552 A | 12/1977 | Going et al. | 128/136 |
| 4,114,614 A | 9/1978 | Kesling | 128/136 |
| 4,337,765 A | 7/1982 | Zimmerman | 128/136 |
| 4,419,992 A | 12/1983 | Chorbajian | 128/136 |
| 4,457,708 A | 7/1984 | Dufour | 433/6 |
| 4,462,800 A | 7/1984 | Jones | |
| 4,471,771 A | 9/1984 | Steven et al. | 128/136 |

(Continued)

FOREIGN PATENT DOCUMENTS

DE        1 566 27        12/1904

(Continued)

OTHER PUBLICATIONS

Supplemental European Search Report dated Mar. 23, 2009, in connection with European Patent Application No. 04 719 238.0, received Apr. 2, 2009.

(Continued)

*Primary Examiner*—Patricia M Bianco
*Assistant Examiner*—Camtu T Nguyen
(74) *Attorney, Agent, or Firm*—Fliesler Meyer LLP (57) ABSTRACT

A mouth guard seated at least partially on an upper jaw of a user to reduce resistance of air flow in a nasal channel of the user comprises a flange positionable between the upper jaw and an associated upper lip such that the flange extends above a gum line of the upper jaw. A chamber within the flange includes a valve for adjusting the volume of the chamber so that pressure applied by the flange to the upper lip is adjustable to affect dilation of the nasal channel resulting from such pressure, thereby allowing the user to selectably reduce resistance of air flow in the nasal channel.

3 Claims, 10 Drawing Sheets

U.S. PATENT DOCUMENTS

| | | | |
|---|---|---|---|
| 4,502,478 A | 3/1985 | Lifton | 128/136 |
| 4,640,273 A | 2/1987 | Greene et al. | 128/136 |
| 4,669,459 A | 6/1987 | Spiewak et al. | |
| 4,715,368 A | 12/1987 | George | |
| 4,755,139 A | 7/1988 | Abbatte et al. | 433/6 |
| 4,765,324 A | 8/1988 | Lake, Jr. | 128/136 |
| 4,791,941 A | 12/1988 | Schaefer | 128/861 |
| 4,810,192 A | 3/1989 | Williams | 433/6 |
| 4,848,365 A | 7/1989 | Guarlotti et al. | 128/859 |
| 4,856,991 A | 8/1989 | Breads et al. | 433/6 |
| 4,867,147 A | 9/1989 | Davis | 128/859 |
| 4,883,072 A | 11/1989 | Bessler | 128/857 |
| 4,901,737 A | 2/1990 | Toone | |
| 4,944,313 A | 7/1990 | Katz et al. | 128/859 |
| 4,955,393 A | 9/1990 | Adell | 128/859 |
| 4,977,905 A | 12/1990 | Kittelsen et al. | 128/861 |
| 5,003,994 A | 4/1991 | Cook | |
| 5,031,638 A | 7/1991 | Castaldi | 128/861 |
| 5,035,613 A | 7/1991 | Breads et al. | 433/6 |
| 5,038,047 A | 8/1991 | Still | 250/516.1 |
| 5,055,039 A | 10/1991 | Abbatte et al. | 433/24 |
| 5,056,534 A | 10/1991 | Wright | 128/848 |
| 5,059,118 A | 10/1991 | Breads et al. | 433/6 |
| 5,063,940 A | 11/1991 | Adell et al. | 128/861 |
| 5,066,226 A | 11/1991 | Summer | |
| 5,067,896 A | 11/1991 | Korn | 433/6 |
| 5,082,007 A | 1/1992 | Adell | 128/861 |
| 5,092,346 A | 3/1992 | Hays et al. | 128/848 |
| 5,103,838 A | 4/1992 | Yousif | 128/859 |
| 5,117,816 A | 6/1992 | Shapiro et al. | |
| 5,152,300 A | 10/1992 | Horst | 128/857 |
| 5,152,301 A | 10/1992 | Kittelsen et al. | 128/861 |
| 5,163,840 A | 11/1992 | Bourke | 433/6 |
| 5,165,424 A | 11/1992 | Silverman | 128/861 |
| 5,174,284 A | 12/1992 | Jackson | 128/200.26 |
| 5,176,514 A | 1/1993 | Viazis | 433/2 |
| 5,186,623 A | 2/1993 | Breads et al. | 433/6 |
| 5,203,351 A | 4/1993 | Adell | 128/859 |
| 5,234,005 A | 8/1993 | Kittelsen et al. | 128/859 |
| 5,235,991 A | 8/1993 | Minneman | 128/859 |
| 5,259,762 A | 11/1993 | Farrell | 433/215 |
| 5,267,862 A | 12/1993 | Parker | 433/215 |
| 5,293,880 A | 3/1994 | Levitt | 128/861 |
| 5,316,020 A | 5/1994 | Truffer | |
| 5,320,114 A | 6/1994 | Kittelsen et al. | 128/861 |
| 5,339,832 A | 8/1994 | Kittelsen et al. | 128/862 |
| 5,353,810 A | 10/1994 | Kittelsen et al. | 128/862 |
| 5,365,945 A | 11/1994 | Halstrom | |
| 5,365,946 A | 11/1994 | McMillan | 128/861 |
| 5,385,155 A | 1/1995 | Kittelsen et al. | 128/861 |
| 5,406,962 A | 4/1995 | Adell | 128/859 |
| 5,406,963 A | 4/1995 | Adell | 128/861 |
| 5,409,017 A | 4/1995 | Lowe | |
| 5,431,563 A | 7/1995 | Huybrechts | 433/48 |
| 5,447,168 A | 9/1995 | Bancroft | 128/859 |
| 5,460,527 A | 10/1995 | Kittelsen | 433/215 |
| 5,469,865 A | 11/1995 | Minneman | 128/859 |
| 5,469,866 A | 11/1995 | Adell et al. | 128/860 |
| 5,499,633 A | 3/1996 | Fenton | 128/848 |
| 5,533,524 A | 7/1996 | Minneman | 128/859 |
| 5,536,168 A | 7/1996 | Bourke | 433/6 |
| 5,566,683 A | 10/1996 | Thornton | |
| 5,566,684 A | 10/1996 | Wagner | 128/861 |
| 5,586,562 A | 12/1996 | Matz | 128/848 |
| 5,624,257 A | 4/1997 | Farrell | 433/6 |
| 5,636,379 A | 6/1997 | Williams | 2/455 |
| 5,665,104 A | 9/1997 | Lee | |
| 5,692,523 A | 12/1997 | Croll et al. | 128/859 |
| 5,727,543 A | 3/1998 | Corsaro | |
| 5,732,715 A | 3/1998 | Jacobs et al. | 128/861 |
| 5,746,221 A | 5/1998 | Jones et al. | 128/859 |
| 5,755,219 A | 5/1998 | Thornton | |
| 5,755,233 A | 5/1998 | Adell | 128/859 |
| 5,794,627 A | 8/1998 | Frantz et al. | |
| 5,810,013 A | 9/1998 | Belfer | |
| 5,816,255 A | 10/1998 | Fishman et al. | 128/861 |
| 5,823,193 A | 10/1998 | Singer et al. | 128/848 |
| 5,876,199 A | 3/1999 | Bergersen | 433/6 |
| 5,884,628 A | 3/1999 | Hilsen | |
| 5,922,006 A | 7/1999 | Sugerman | |
| 5,924,422 A | 7/1999 | Gustafson | 128/846 |
| 5,931,164 A | 8/1999 | Kiely et al. | 128/859 |
| 5,941,246 A | 8/1999 | Roopchand | 128/207.14 |
| 5,947,918 A | 9/1999 | Jones et al. | 602/58 |
| 5,970,981 A | 10/1999 | Ochel | 128/859 |
| 5,979,449 A | 11/1999 | Steer | 128/848 |
| 6,003,515 A | 12/1999 | Maness | 128/857 |
| 6,036,487 A | 3/2000 | Westerman | 433/6 |
| 6,080,923 A | 6/2000 | Austin | 84/383 R |
| 6,082,363 A | 7/2000 | Washburn | 128/859 |
| 6,089,864 A | 7/2000 | Buckner et al. | 433/71 |
| 6,092,524 A | 7/2000 | Barnes, Sr. | 128/859 |
| 6,098,627 A | 8/2000 | Kellner et al. | 128/859 |
| 6,109,265 A | 8/2000 | Frantz et al. | |
| 6,109,266 A | 8/2000 | Turchetti | 128/861 |
| 6,129,084 A | 10/2000 | Bergersen | 128/848 |
| 6,164,278 A | 12/2000 | Nissani | 128/848 |
| 6,170,485 B1 | 1/2001 | Orrico | |
| 6,318,371 B1 | 11/2001 | Tyszkiewicz | 128/859 |
| 6,321,752 B1 | 11/2001 | Spottiswoode | 128/859 |
| 6,325,064 B1 | 12/2001 | Thornton | |
| 6,328,754 B1 | 12/2001 | Marten et al. | |
| 6,375,667 B1 | 4/2002 | Ruch | |
| 6,390,089 B1 | 5/2002 | Lacouture | |
| 6,397,848 B1 | 6/2002 | Kagekata et al. | 128/862 |
| 6,405,729 B1 | 6/2002 | Thornton | |
| 6,412,489 B1 | 7/2002 | Sue | 128/848 |
| 6,446,631 B1 | 9/2002 | Hagiwara | |
| 6,450,167 B1 | 9/2002 | David et al. | |
| 6,478,023 B1 | 11/2002 | Lockwood | |
| 6,491,036 B2 | 12/2002 | Cook | 128/859 |
| 6,491,037 B1 | 12/2002 | Mortenson | 128/859 |
| 6,491,521 B1 | 12/2002 | Fowler, Jr. | 433/167 |
| 6,494,210 B1 | 12/2002 | Mams | 128/859 |
| 6,505,626 B2 | 1/2003 | Kittelsen et al. | 128/859 |
| 6,505,627 B2 | 1/2003 | Kittelsen et al. | 128/859 |
| 6,505,628 B2 | 1/2003 | Kittelsen et al. | 128/859 |
| 6,508,251 B2 | 1/2003 | Kittelsen et al. | 128/859 |
| 6,510,853 B1 | 1/2003 | Kittelsen et al. | 128/859 |
| 6,516,805 B1 | 2/2003 | Thornton | |
| 6,553,569 B2 | 4/2003 | Bush | 2/9 |
| 6,553,996 B2 | 4/2003 | Kittelsen et al. | 128/859 |
| 6,581,604 B2 | 6/2003 | Cook | 128/859 |
| 6,584,978 B1 | 7/2003 | Brett et al. | 128/859 |
| 6,588,430 B2 | 7/2003 | Kittelsen et al. | 128/859 |
| 6,637,436 B2 | 10/2003 | Farrell | 128/861 |
| 6,675,806 B2 | 1/2004 | Kittelsen et al. | 128/859 |
| 6,675,807 B2 | 1/2004 | Kittelsen et al. | 128/859 |
| 6,675,808 B2 | 1/2004 | Karasic | 128/859 |
| 6,681,771 B2 | 1/2004 | Durette | 128/859 |
| 6,691,710 B2 | 2/2004 | Kittelsen et al. | 128/859 |
| 6,769,910 B1 | 8/2004 | Pantino | 433/6 |
| 6,802,079 B2 | 10/2004 | Bush | 2/9 |
| 6,805,127 B1 | 10/2004 | Karasic | 128/861 |
| 6,820,617 B2 | 11/2004 | Robertson et al. | 128/204.18 |
| 6,820,623 B2 | 11/2004 | Cook | 128/859 |
| 6,837,246 B1 | 1/2005 | DeLuke | 128/860 |
| 6,851,424 B2 | 2/2005 | Scopton | 128/200.26 |
| 6,886,567 B1 | 5/2005 | Liu | 128/861 |
| 6,932,087 B1 | 8/2005 | Burns | 128/859 |
| 6,932,088 B1 | 8/2005 | Berghash | 128/861 |
| 6,935,857 B1 | 8/2005 | Farrell | 433/6 |
| 6,941,952 B1 | 9/2005 | Rush, III | 128/861 |
| 6,951,678 B2 | 10/2005 | Takeshita et al. | 428/64.1 |

| | | |
|---|---|---|
| 6,986,354 B1 | 1/2006 | Burns .......... 128/859 |
| 7,077,646 B2 | 7/2006 | Hilliard .......... 433/6 |
| 7,128,072 B2 | 10/2006 | Bancroft .......... 128/859 |
| 7,175,427 B2 | 2/2007 | Smith .......... 433/9 |
| 7,178,520 B2 | 2/2007 | Scopton .......... 128/200.26 |
| 7,178,529 B2 | 2/2007 | Kownacki |
| 7,182,086 B2 | 2/2007 | Fujieda et al. .......... 128/862 |
| 7,210,483 B1 | 5/2007 | Lesniak et .......... 128/861 |
| 7,255,108 B1 | 8/2007 | Loughlin .......... 128/848 |
| 7,299,804 B2 | 11/2007 | Kittelsen et al. .......... 128/859 |
| 7,328,705 B2 | 2/2008 | Abramson |
| 7,328,706 B2 | 2/2008 | Bardach et al. .......... 128/861 |
| 7,353,828 B1 | 4/2008 | Hirshberg .......... 128/861 |
| 7,404,403 B2 | 7/2008 | Farrell .......... 128/859 |
| 7,404,404 B2 | 7/2008 | Lombardi .......... 128/861 |
| 7,422,017 B2 | 9/2008 | Bancroft .......... 128/859 |
| 7,481,773 B1 | 1/2009 | Dorroh et al. .......... 600/549 |
| 7,506,651 B2 | 3/2009 | Anonsen .......... 128/859 |
| 7,530,355 B2 | 5/2009 | Berghash .......... 128/861 |
| 7,549,423 B1 | 6/2009 | Hirshberg .......... 128/861 |
| 7,581,542 B2 | 9/2009 | Abramson |
| 2004/0013993 A1 | 1/2004 | Ito |

FOREIGN PATENT DOCUMENTS

| | | |
|---|---|---|
| DE | 2 320 501 | 11/1974 |
| DE | 3 707 952 | 9/1988 |
| EP | 0 312 368 | 10/1988 |
| EP | 0 359 135 | 3/1990 |
| EP | 0 801 937 | 10/1997 |
| GB | 1 569 129 | 6/1980 |
| GB | 2 264 868 | 9/1993 |
| WO | 98/51234 | 11/1998 |

OTHER PUBLICATIONS

Truitt, J. Wellington, Jr., B.S. D.D.S., The Frankel Appliance, Advanced Orthopedic and Orthodontic Therapy, Chapter 7, Clinical Foundation of Orthodontics and Orthopedics, P.O. Box 130, Gainesville, Texas 76240, USA.

Moyers, Robert E., Handbook of Orthodontics for the Student and General Practitioner 669 (3rd ed. 1973).

Dentaurum, Lip Bumpers Model 748-009-00 and 748-114-00, http://www.gacintl.com/onlinecat_a.html, p. 143, Catalog 12 is first documented by a web archival service (waybackmachine.org) on Jun. 4, 2004.

Cetlin Ideal Lip Bumper and Molded Lip Bumper, http://www.gacintl.com/onlinecat_a.html, p. 74, Catalog 12 is first documented by a web archival service (waybackmachine.org) on Jun. 4, 2004.

Not submitted because it was submitted in prior U.S. Appl. No. 11/485,942, filed Jul. 13, 2006, relied on under 35 USC §120.

* cited by examiner

MOUTH GUARD INCLUDING NASAL DILATOR FOR IMPROVED BREATHING

CLAIM OF PRIORITY

This Application is a Continuation of U.S. patent application Ser. No. 11/485,942, now U.S. Pat. No. 7,581,542, entitled "METHOD FOR TREATING SLEEP APNEA," filed Jul. 13, 2006, which is a Divisional of application Ser. No. 10/386,063, now U.S. Pat. No. 7,328,705, entitled "DENTAL APPLIANCE FOR IMPROVING AIRFLOW THROUGH NASAL-PHARYNGEAL AIRWAY," filed Mar. 10, 2003, both of which are hereby incorporated by reference herein.

BACKGROUND OF THE INVENTION

1. Field of Invention

This invention relates to a nasal dilator, particularly to such a device which is designed to reduce airway resistance and therefore aid air flow through both the nasal and posterior pharyngeal regions of the upper airway.

2. Discussion of the Prior Art

Upper airway resistance to airflow is an affliction which affects millions of individuals and has very serious medical consequences with significant morbidity and mortality. The health effects are brought about by the disruption of normal sleep of those afflicted with snoring and sleep apnea (complete stoppage of breathing for a period of time). The effects of snoring and sleep apnea may also compromise the well being of those sleeping in proximity to the afflicted person by disrupting their ability to achieve healthy, restful sleep.

Sleep is impacted by both the increased effort needed to overcome increased resistance to airflow and by the fragmentation of sleep patterns brought about by awakenings that occur in both hyponia (reduced air flow) and apneic events (periods of stoppage of air flow). These conditions limit one's ability to go into the deeper stages of sleep that are necessary to refresh and restore and are damaging to many body systems.

The primary treatment for snoring and apnea is the use of a device, referred to as a CPAP (Continuous Positive Air Pressure) device. This device delivers pressurized air from a pumping component through a hose to a mask which is secured over the nose of the individual. This is successful at correcting the problem but is not well tolerated by a significant group of individuals due to the discomfort, lifestyle issues, and difficulty in the portability in traveling with the CPAP. Because of these factors a significant number of patients are forced to abandon the use of this therapy.

Surgical techniques have been available for many years; these attempt to permanently correct snoring problems encountered by individuals. However such surgical procedures are complicated and invasive and sometimes permanently change the appearance of the individual. In addition, numerous medical drawbacks, including cost, irreversibility, surgical risk, and long painful recovery periods, are inherent in surgical procedures.

Numerous devices are known which attempt to alleviate or eliminate snoring problem without invasive surgery. Some devices have focused on improving airflow through the nose. These devices are used both in awake periods, during increased demand such as athletic usage, and during sleep to improve airflow as an anti-snoring device.

There are two mechanisms: one attaches to the external skin of the nose on the right and left sides of by means of adhesives which act by pulling the skin outward to strengthen and expand the nasal passages. (Ruch, U.S. Pat. No. 6,375,667, Apr. 23, 2002) This device is disposable and can irritate the skin. Other such devices are designed to fit inside the nasal passageway and push the inner walls of the nose out, expanding the air passage. (Corsaro, U.S. Pat. No. 5,727,543, Mar. 17, 1998). This device can irritate the sensitive inner lining of the mucosa of the nasal passageway and is awkward.

There are also numerous devices known which attempt to alleviate or eliminate snoring problems without invasive surgery by repositioning the lower jaw (mandible) in an anterior (forward) direction. This pulls the base of the tongue forward and thereby increases the air passage in the posterior pharyngeal region (breathing passage behind the base of the tongue).

Devices which bring the mandible forward into a functional repositioning posture, and which hold the posterior airway open, fall into two general categories. The first is non-adjustable: the device fits in the mouth at a prescribed position. The disadvantage of this is that there are changes over time that occur and therefore may require changing the position of the lower jaw in relationship to the upper jaw over a period of time.

Devices which are adjustable have significant components inside the mouth behind the teeth. They take up space inside the mouth, restricting the space for the tongue and preventing it from coming forward. Some devices also have projections which extend from the mouth out between the lips. These affect the user's ability to close their lips, making the appliance less comfortable and inhibiting the ability of the user to turn to different positions during sleep.

Thus all known devices and techniques for improving airflow have one or more drawbacks or disadvantages.

OBJECTS AND ADVANTAGES

Accordingly several objects and advantages of the present invention are:
(a) to provide an improved device for improving air flow through the nasal and pharyngeal air passage, preventing snoring and sleep apnea.
(b) To provide such a device that acts as a single unit and which works in a synergistic system
(c) to provide a nasal breathing aid which acts intraorally and can be fixed in place by attachment to a device,
(d) to provide an anti-snoring device which maintains maximum intraoral tongue space,
(e) to provide such a device which is entirely contained within the oral cavity and does not extend out between the lips Further objects and advantages are:

Still further, to provide a device for improved nasal breathing and providing additional protection from traumatic injury which is incorporated into athletic mouth guards.

Still further, to provide a mandibular repositioning device that can be used in orthodontic therapy.

Yet further objects and advantages will become apparent from a reading of the ensuing descriptions and accompanying drawings.

SUMMARY

In accordance with this invention I provide a device for improving airflow for breathing by stretching the skin of upper lip region and the nose to maintain the free flow of air through the nasal air passage. The device comprises a base element that anteriorly repositions the lower jaw, thus repositioning the base of the tongue anteriorly. This reduces the resistance of airflow through the pharyngeal region by preventing the tongue from falling back during sleep and obstructing the pharyngeal airway located in back of the tongue region.

DRAWINGS—REFERENCE NUMERALS

| | |
|---|---|
| 10 thermoplastic base unit | 12 right posterior section |
| 14 left posterior section | 16 right lateral wall |
| 18 left lateral wall | 20 left occlusal wall |
| 22 right occlusal wall | 24 right lingual wall |
| 26 left lingual wall | 27 anterior lingual flange |
| 28 right occlusal laminate | 29 left occlusal laminate |
| 30 right attachment tube | 31 right outer tube |
| 32 left attachment tube | 34 left outer tube |
| 36 right retention plate | 37 left retention plate |
| 38 right orthodontic adjustment screw | 40 left orthodontic adjustment screw |
| 42 right acrylic head wall | 44 left acrylic head wall |
| 46 acrylic material joining screw to base | 50 right connecting/adjustment wire |
| 52 left connecting/adjustment wire | 54 right adjustment section |
| 56 left adjustment section | 58 right upper-horizontal wire |
| 60 left upper-horizontal wire | 62 right distal-vertical wire |
| 64 left distal-vertical wire | 66 right lower-horizontal wire |
| 68 left lower-horizontal wire | 70 right anterior-vertical wire |
| 72 left anterior-vertical wire | 74 right body of connecting wire |
| 76 left body of connecting wire | 78 right vertical rise of connecting wire |
| 80 left vertical rise of connecting wire | 82 right anterior face of connecting wire |
| 84 left anterior face of connecting wire | 86 maxillary flange |
| 88 right nasio-labial dilator buttons | 90 left nasio-labial dilator buttons |
| 92 nasio-labial dilator body wire | 94 right button retention loop |
| 96 left button retention loop | 98 right free wire segment |
| 100 left free wire segment | 102 attachment segment |
| 104 maxillary dental splint | 110 acrylic bonding material |
| 112 maxillary repositioning flange | 114 anterior segment of expansion screw |
| 116 adjustment segment of expansion screw | 118 posterior segment of expansion screw |
| 120 acrylic attachment of expansion screw | 122 moveable wall of expansion screw |
| 124 adjustment nut | 126 mouth guard nasal extension |
| 128 injection valve | 130 fluid/air chamber |
| 132 mouth guard | |

DETAILED DESCRIPTION

FIGS. 1-4

Figure 1:
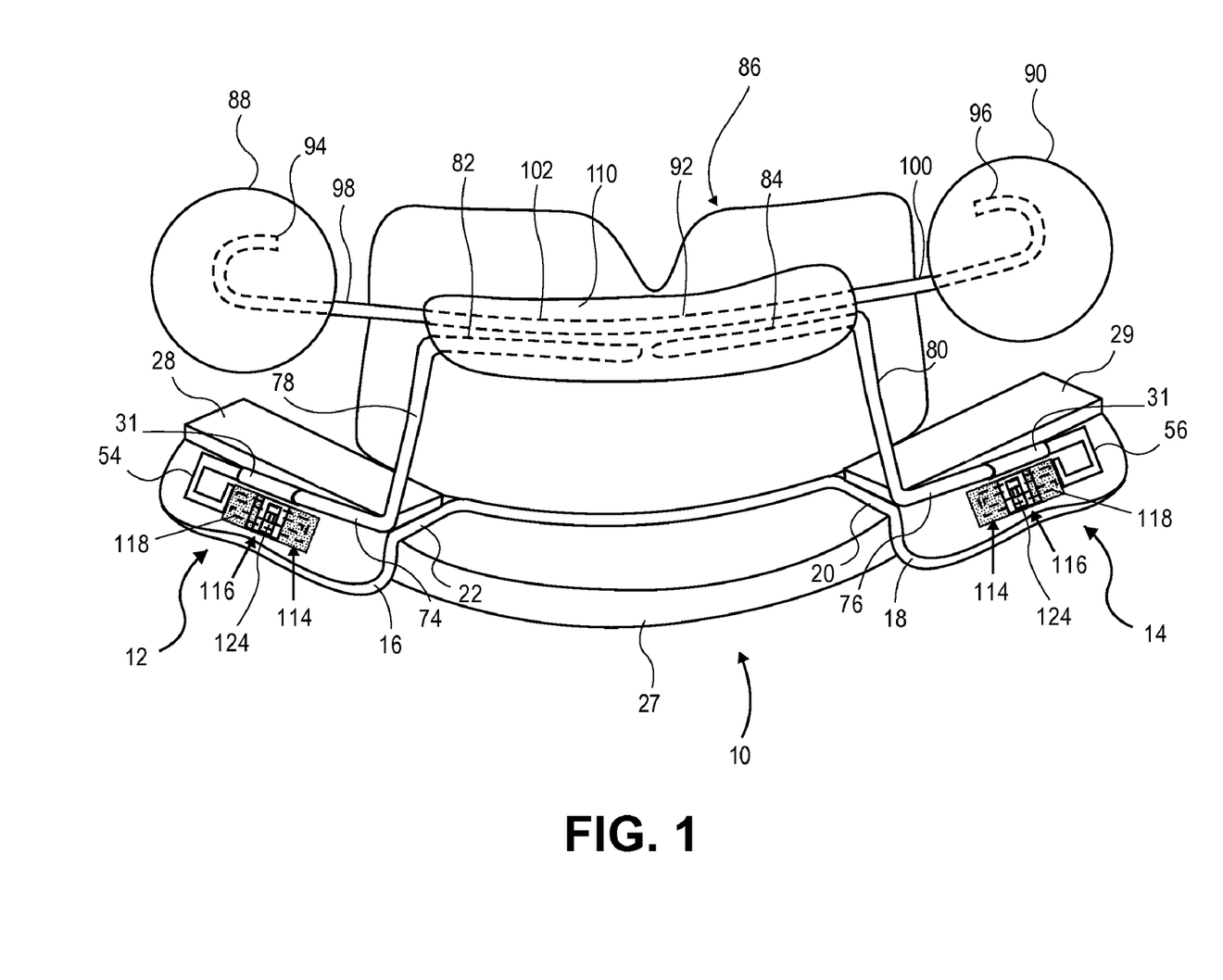
FIG. 1 shows a front view of a device for nasal dilation and anti-snoring according to my invention.
Figure 2:
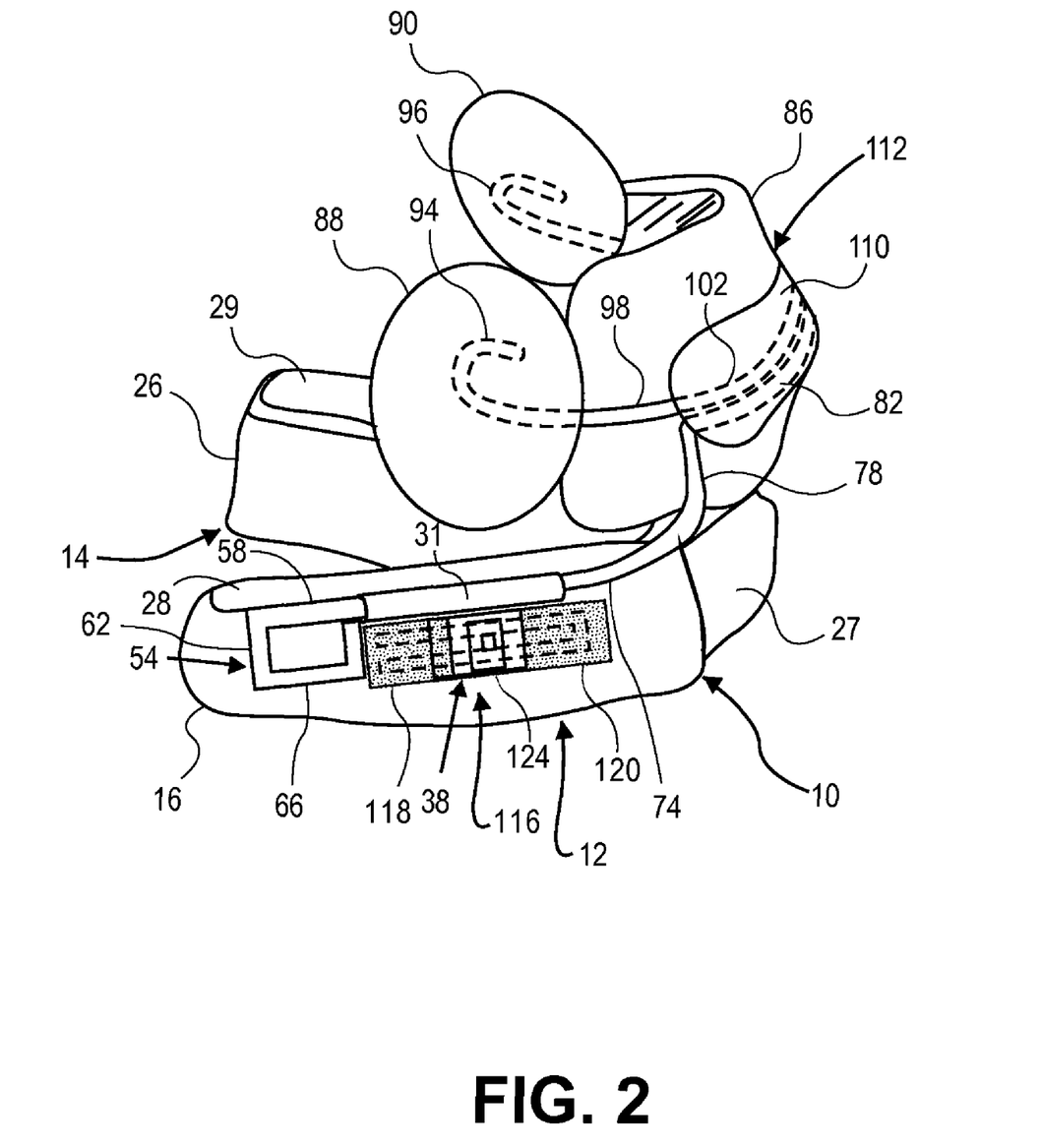
FIG. 2 shows a lateral view of the device in FIG. 1.
Figure 3:
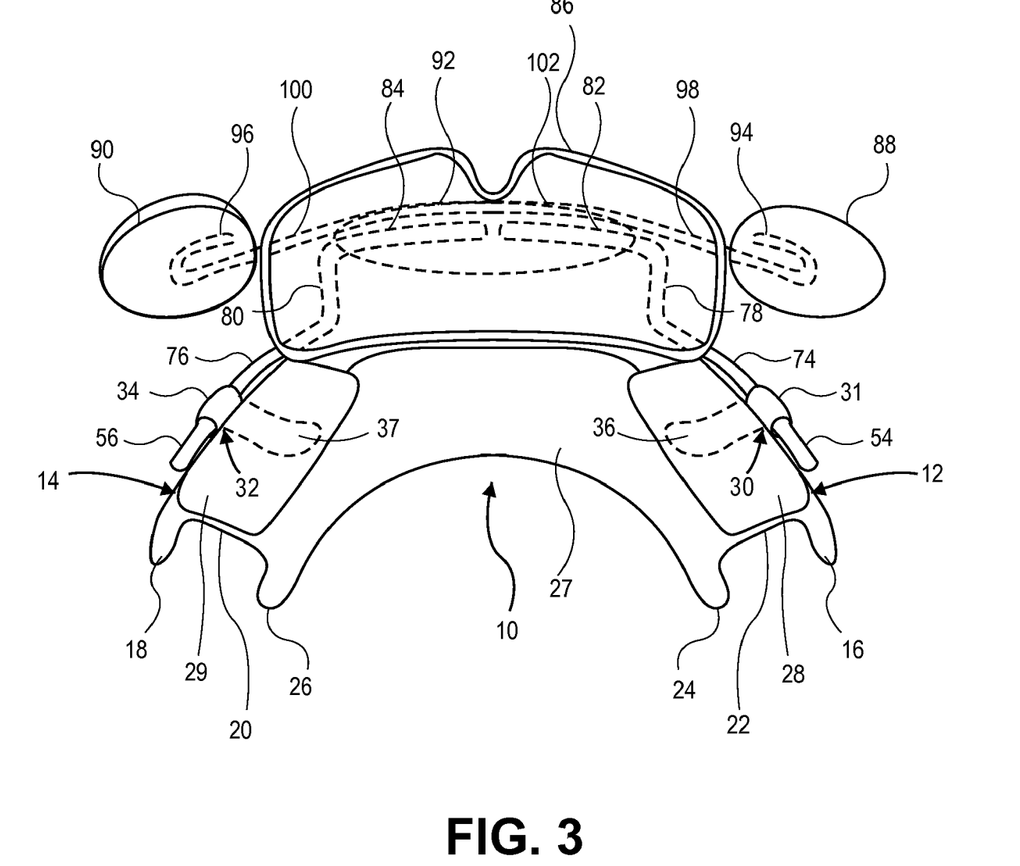
FIG. 3 shows a posterior view of the device in FIG. 1.
Figure 4:
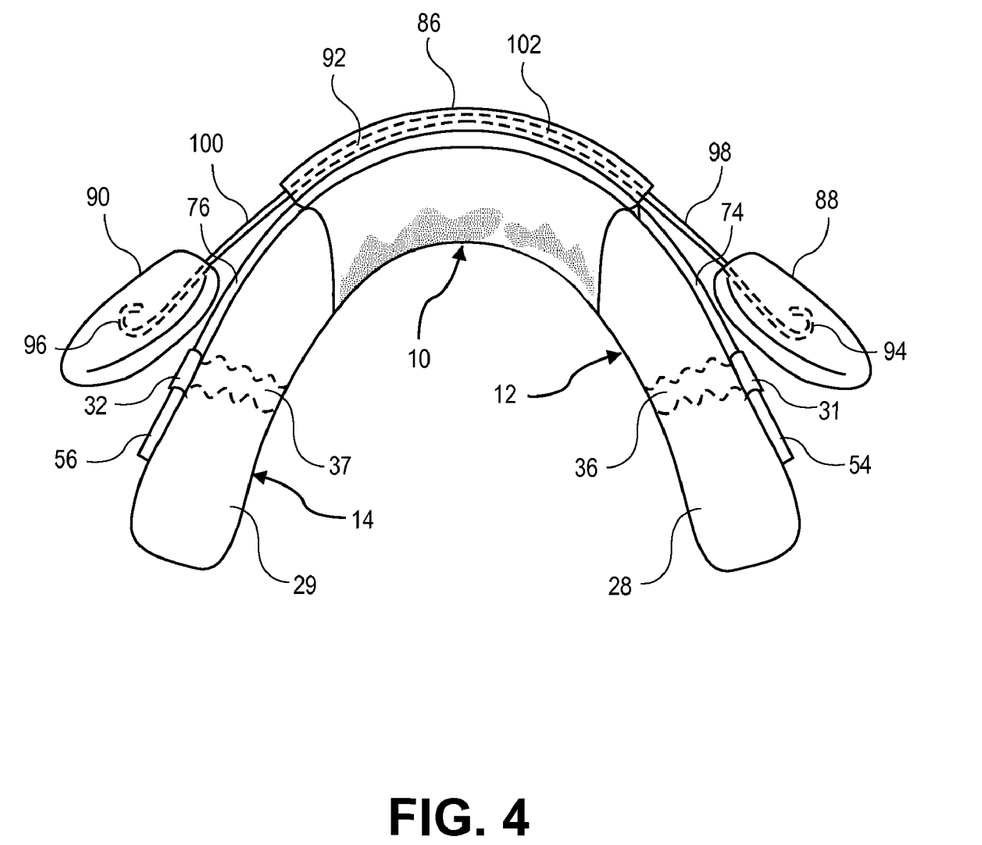
FIG. 4 shows a superior view of the device in FIG. 1.
Figure 5A:
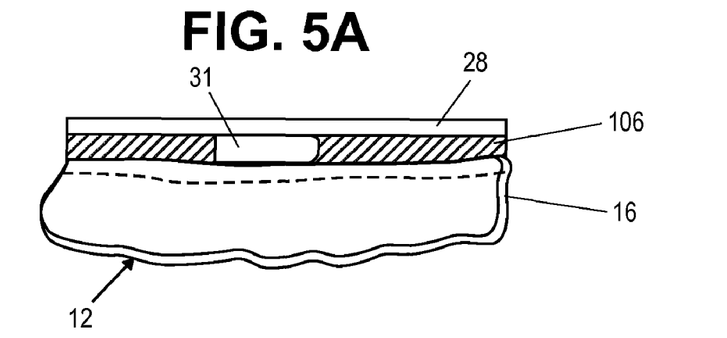
FIGS. 5A-5D show various aspects of an adjustable attachment of a lower base section of the device of FIG. 1.
Figure 5B:
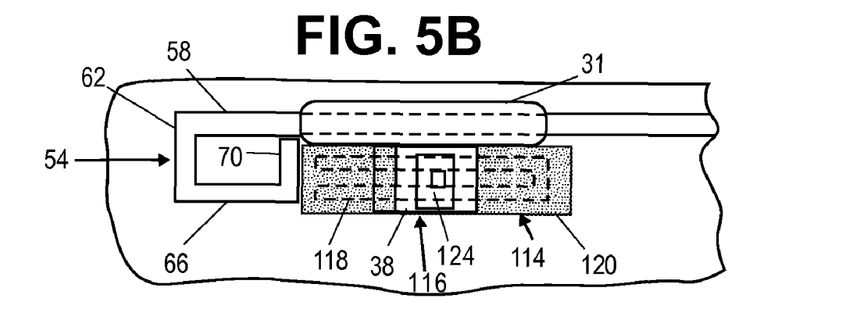
Figure 5C:
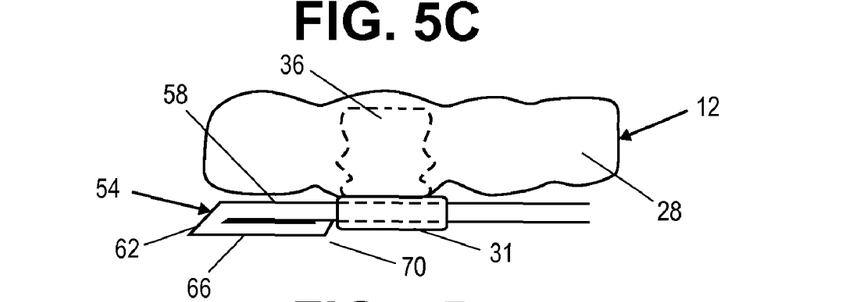
Figure 5D:
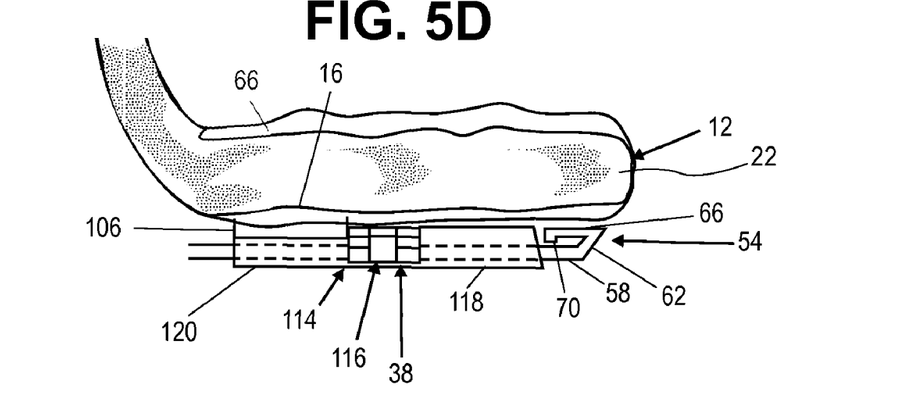

A preferred embodiment of a nasal dilator and anti-snoring device according to the invention is illustrated and FIG. 1 (anterior view), FIG. 2 (lateral view), FIG. 3 (posterior view), and FIG. 4 (top view). The device has a base unit 10, which fits over the lower teeth. It is constructed of thermoplastic material, which is heat molded over a dental model of the patient's teeth. In the preferred embodiment, the thermoplastic material used is 3 mm thick biocryl, available from Great Lakes Orthodontics of Tonawanda, N.Y. The biocryl is pressure molded over the dental casts of the lower teeth using a Biostar thermoplastic molding unit, available through Great Lakes Orthodontics.

The resultant molded form is cut in the inner side (lingual/tongue) of the dental arch approximately 3-5 mm below the upper margin of the gum line from the back of the posterior-most tooth on the right completely around the dental arch to the posterior-most tooth on the left. The molded material is then cut around the outer gingival margin of the molar and bicuspid teeth so that the material forms a right posterior section 12 with a right lateral wall 16, a right occlusal wall 22, and right lingual wall 24, all of which encase the posterior teeth.

The device has a left posterior section 14, which is cut in a similar fashion providing a left lateral wall 18, a left occlusal wall 20, and a left lingual wall 26, which provide encasement of the left posterior teeth.

The posterior sections provide coverage of the teeth and a means of securing base unit 10 to the dental arch. The molded biocryl material is next cut to remove the material on the facial or outer surface of the anterior teeth from the right canine tooth to the left canine tooth, leaving an anterior lingual flange 27 which extends from the inside upper edges of the anterior teeth to 3-5 mm below the gum-tooth margin. This completes base unit 10.

Base unit 10 can also be made of any other material which can be used to secure the lower dental arch, such as processed acrylics, hard-molded outer shell material with a soft inner lining, boil-and-bite materials, preformed arch forms, or other commercially available materials.

Orthodontic headgear tubes, available from Posse Dental Supply of Oxnard, Calif., are used as right and left attachment tubes 30 and 32. Tubes 30 and 32 consists of outer tubes 31 and 34 and right and left retention plates 36 and 37. Tubes 30 and 32 are placed over occlusal walls 20 and 22 so that retention plates 36 and 37 lie across the top of occlusal walls 20 and 22 at the area of the first molar tooth. This creates right and left tubes 30 and 32 which are oriented so that retention plates 36 and 37 lie over the occlusal walls and outer tubes 31 and 34 are cantilevered out laterally. Other means of attachment may be used, such as snap mechanisms and bonding of the joining mechanisms.

FIGS. 5A-5D—Posterior Lower Base With Adjustment Components

FIGS. 5A-5D show various views of posterior sections 12 and 13. Occlusal laminates for right and left sides 28 and 29 are made by cutting a piece of 1 mm biocryl to fit over right and left occlusal walls 20 and 22, respectively. Each layer of occlusal laminates 28 and 29 is bonded to respective occlusal walls 20 and 22 by a layer of cold-cure acrylic. Plates 36 and 37 are bonded into their positions over the first molar region lying between occlusal laminates 28 and 29 and occlusal walls 20 and 22, respectively. Multiple layers or greater thicknesses of material can be used to increase the height of base unit 10.

An orthodontic adjusting screw—in the preferred embodiment a 3 mm Forestadent Standard Expansion Screw, available from Great Lakes Orthodontics—is used. Orthodontic acrylic is applied to cover the posterior segment of the expansion screw 118 to form a posterior acrylic adjustment wall 122. The screw is positioned on lateral wall 16 below outer tube 31 so that adjustment wall 122 butts up against anterior-vertical wire 70. Orthodontic acrylic is applied to the anterior segment of the expansion screw 114, bonding it to lateral wall 16. The adjustment segment of expansion screw 116 and the posterior segment of expansion screw 118 remain unattached and free to move.

Adjustment segment of expansion screw 116 can be adjusted by a key (not shown). The key is a straight wire which can be inserted into a hole in adjustment nut 124 and used as a lever to rotate nut 124. As nut 124 turns it expands the adjustment section 116, moving the free posterior segment of the expansion screw 118 in a posterior direction. This pushes adjustment wire 50 moving it in a posterior direction through outer tube 31, carrying the repositioning flange 112 in a posterior direction. This adjustment is used to reposition the lower jaw forward relative to the upper jaw to increase the repositioning effect of the device.

This process is repeated on the left side of the device.

A length of orthodontic wire is used as a right connecting and adjustment wire 50. In the preferred embodiment, Leone orthodontic wire, which is 1.1 mm in diameter, available from Posse Dental Supply, is used.

Wire 50 is bent 3 to 4 mm from its end at a 90-degree angle using orthodontic pliers to form right anterior-vertical wire 70. Another bend is made 3 to 4 mm from the initial bend in a 90-degree angle around parallel axis from the first bend so as to form a right lower-horizontal wire 66. A third 90-degree bend is made 3 to 4 mm from the second and around a parallel axis to the first two bends to form a right distal-vertical wire 62. This configuration forms right adjustment section 54.

Another length of orthodontic wire is cut and bent in the same manner as wire 50 to form a left connecting-adjustment wire 52 and corresponding left adjustment section 56 with its corresponding left upper-horizontal wire 60, left distal-vertical wire 64, left lower-horizontal wire 68 and left anterior-vertical wire 72. However the number of bends in right connecting-adjustment wire 50 and 52 can be reduced so that there is a 90-degree bend 8 mm from the end of the wire. A 180-degree foldback bend is made 4 mm in from the end of the wire to create right adjustment section 54 with a right anterior-vertical wire 70 and a right distal-vertical wire 62.

Right wire 50 is inserted into the back of right outer tube 31 so that adjustment section 54 is distal to outer tube 31 and right body of connecting wire 74 passes through the tube and extends anteriorly. At the junction of the first premolar and the canine tooth, a 90-degree bend is made parallel to the axis of the bands of adjustment section 54, forming right vertical rise of connecting wire 78. Another 90-degree bend is made so that the portion of wire anterior to right vertical rise of connecting wire 78 is directed towards the curve of the anterior dental arch, forming a right anterior face of connecting wire 82. Face 82 is bent to form a curve around the anterior dental arch.

Left connecting-adjustment wire 52 is inserted into left outer tube 34 and corresponding bends are made to form left body of connecting wire 76 of the left vertical rise of connecting wire 80 and the left anterior face of connecting wire 84. Left and right anterior faces of connecting wires 82 in 84 meet at the midline.

Figure 6:
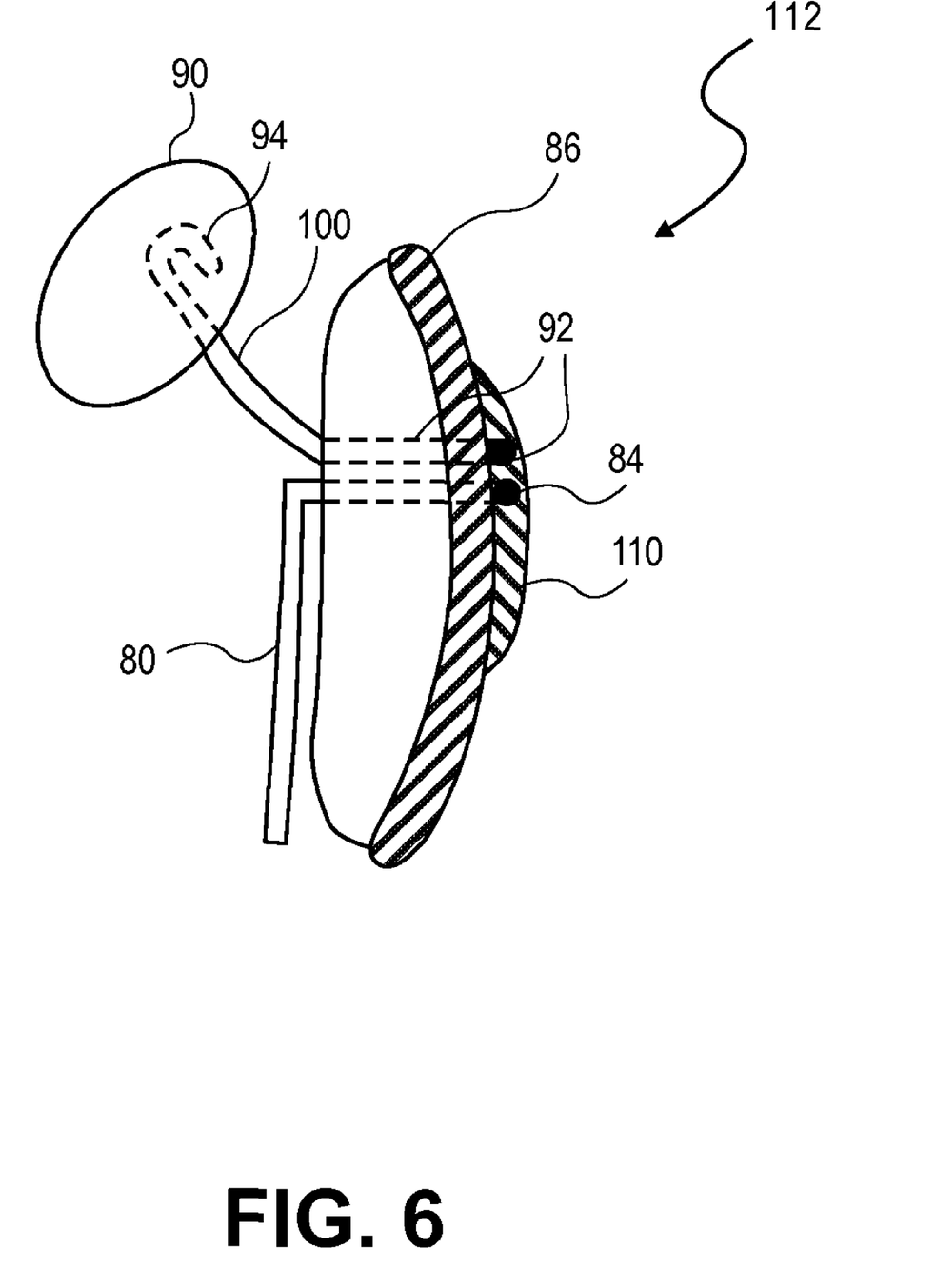
FIG. 6 shows a midline cut view through the center of an upper anterior section of the device of FIG. 1.

FIG. 6—Midline Cut View Upper Segment

FIG. 6 shows a midline cut view of maxillary repositioning flange 112.

A sheet of thermoplastic material is molded over the cast of the upper dental arch of the patient. In the preferred embodiment a 1 mm sheet of biocryl is used. However, other materials may be used, as discussed A separating media sheet is molded over splint 104 and a sheet of 3 mm biocryl is heat molded over the facial surface of the anterior of the splint 104 and the separating media. This molded material is removed and cut so that it extends from the junction of the first bicuspid tooth and the canine tooth on one side to the junction of the first bicuspid tooth and canine tooth on the opposite side and form the edges of the anterior teeth up to the uppermost vestibular extension to form a maxillary flange 86.

Figure 7A:
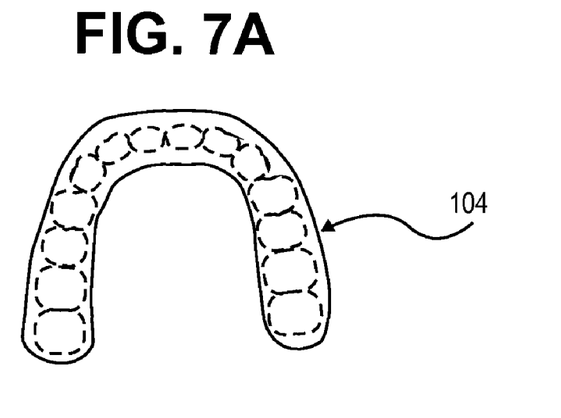
FIG. 7A shows a view looking down on upper dental splint.
Figure 7B:
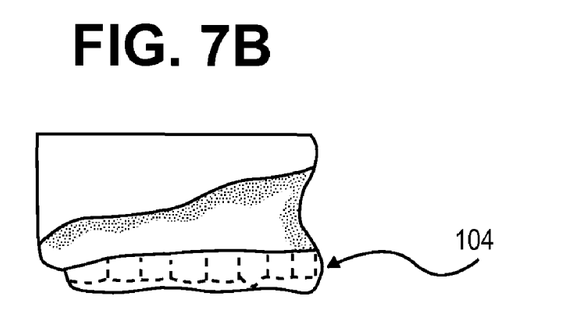
FIG. 7B shows a lateral view of upper dental splint in place on a dental cast.

FIGS. 7A-7B—Upper Splint

FIG. 7A shows the maxillary dental splint 104 as seen looking down into the inner surface of splint and FIG. 7B shows the dental splint placed on a dental cast.

The sheet of biocryl, which has been molded over the upper dental cast, is cut so that it extends over the dentition up to the gingival margins to form maxillary dental splint 104. Splint 104 is placed in position over the occlusal side of base unit 10 and positioned so that the midline of the teeth lines up and the dental arch is oriented so that the lower anterior teeth provide 1 to 3 mm forward of the upper anterior teeth. It can be positioned by using a dental cast mounted on an articulator using a bite registration taken on the patient in the desired position to orient the dental casts on an articulator alternatively it can be estimated and then adjusted on delivery.

Flange 86 is placed in position anterior to maxillary splint 104 so that it fits between splint 104 and wires 82 and 84. Orthodontic acrylic is applied over wires 82 and 84, joining them to flange 86. The bulk of orthodontic acrylic material used to attach wires 82 and 84 that extend out from flange 86 to form an acrylic bumper 110. This unit forms maxillary repositioning flange 112.

A length of orthodontic wire, in the preferred embodiment a 10 cm length of 1.2 mm diameter Leone wire is used. A right button retention loop 94 is bent at one end and a left button retention loop 96 is bent on a parallel axis so that the final length of wire is equal to the circumference of the dental arch from the lateral of the canine root area on the right side to the lateral to canine root area on left side. This is usually approximately 8 cm in length.

Two nasio-labial dilator buttons 88 are made by placing liquid orthodontic acrylic into previously made molds, which have a smooth spherical facial surface and a flat back surface. Buttons 88 are placed on a counter with the spherical surface facing down in a pre-made rubber mold. A nasio-label dilator body wire 92 is placed on top of the flat surfaces of buttons 88 so that their loops 94 and 96 are centered over the flat surface of buttons 88. Buttons 88 are bonded to loops 94 and 96 by means of orthodontic acrylic, which is applied over the buttons, embedding the wire and bonding it to buttons 88. This forms a nasal dilator apparatus 87.

Nasal dilator apparatus 87 is made to fit over maxillary flange 86 by creating a band in body wire 92, which forms to the facial surface of flange 86. Nasal dilator apparatus 87 is centered on the upper facial surface of maxillary flange 86. Orthodontic acrylic is applied over the center portion of the wire laterally to the lateral incisor area to join nasal dilator apparatus 87 to maxillary flange 86. Nasal dilator apparatus 87 has right and left free wire segments 98 and 100, which allow adjustment of buttons 88 and 90 to position them in the vestibule at the correct height and distance from the maxilla. This creates the appropriate stretching of the upper lip and lateral nasal walls to maintain and stretch, therefore increase the nasal canal to allow freer flow of air.

Figure 8:
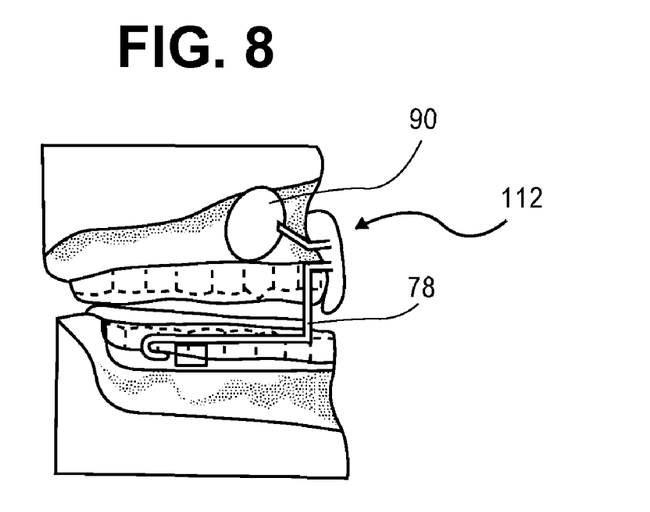
FIG. 8 shows a lateral view of the device in FIG. 1 on dental models.

Operation—FIG. 8—Device In Place On Dental Models

FIG. 8 shows the device in position on a dental cast as it sits over the teeth in the mouth. It positions and holds the lower jaw forward. This forward posturing of the mandible prevents the jaw and tongue from moving posteriorly, thus preventing the patient's airway from being compromised.

The user wears this device by placing it in their mouth as they are going to sleep. Maxillary dental splint 104 sits over the upper teeth to support the teeth and distribute the forces of the mandible throughout the dental arch. Splint 104 is then snapped in over the teeth and is held secure by the frictional force of the material around the teeth.

Specifically, the device is placed in the mouth with lower dental arch secured in place by means of base unit 10 over the lower dental arch and engaging it by snapping it over the teeth. Maxillary repositioning flange 112 is positioned anterior to the maxillary dental arch with the maxillary splint. It is necessary for the patient to reposition their mandible forward as the lower jaw is closed in order to position maxillary repositioning flange 112 in its proper functional position in front of the upper anterior teeth. The device then holds the mandible in a more forward position and helps maintain the airway patent while allowing a degree of mobility of the jaw.

Nasal dilator apparatus 87 is positioned inside the upper lips and stretches the lips to maintain the nasal air channel patent.

Gross adjustments of the mandibular repositioning can be made by bending right and left adjustment sections 54 and 56 in a manner which pushes anterior vertical wires 70 and 72 anterior or posterior to their original position. More sensitive adjustments can be made by adjusting expansion screw assembly 116 and expanding the screw, thereby pushing adjustment wire sections 54 and 56. Both of these methods of adjustment act by moving adjustment wires 50 and 52 and maxillary repositioning flange 112 in a posterior direction, therefore moving the mandible in a more anterior direction.

Nasal dilator apparatus 87 can be adjusted by bending free wire segments 98 and 100 to alter the position of buttons 88 so that they cause stretching of the nasal labial tissue. This stretch increases the tension of the lateral walls of the nose, increasing the strength of these walls against the collapsing forces of inspiration. This allows air to move through the nasal passage with greater ease, resulting in greater airflow and a lessening of the negative pressure created in inspiration. Decreasing the negative pressure in the nasal region decreases it in the entire respiratory channel and works with the mandibular repositioning to improve the function of the device.

Figure 9A:
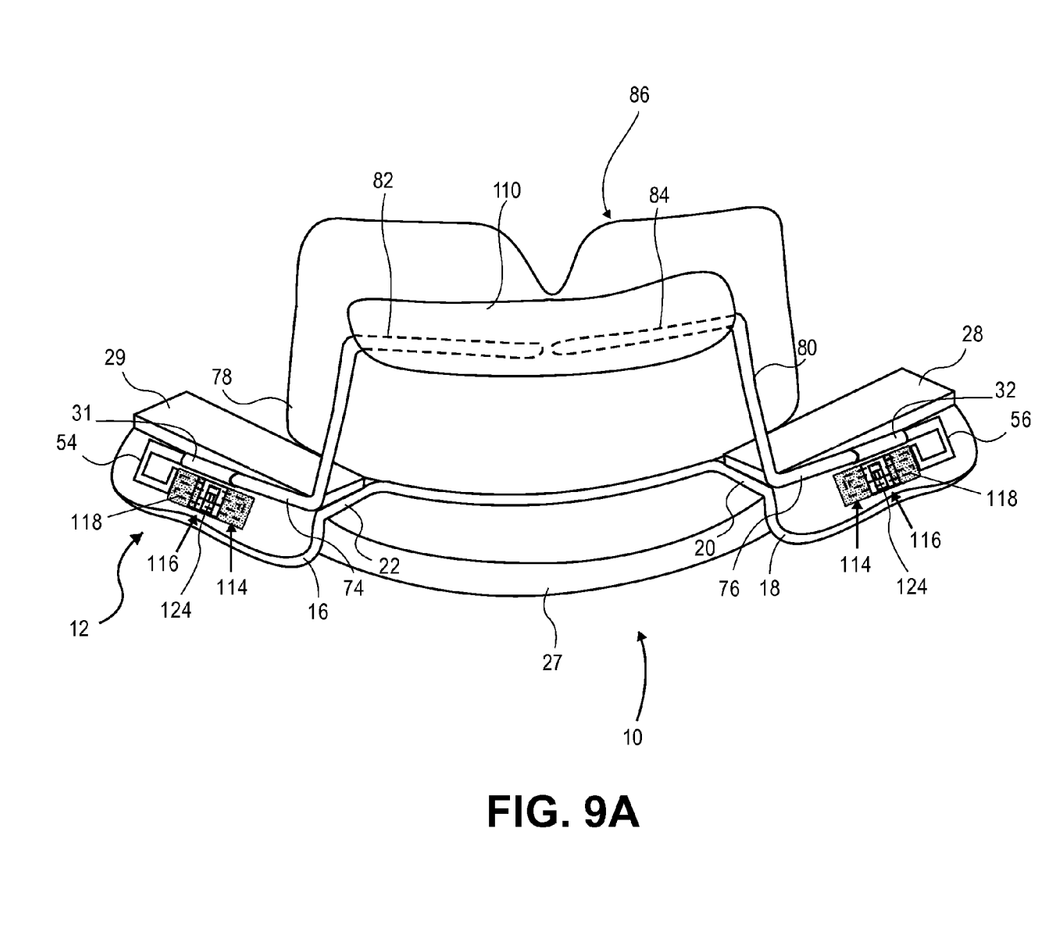
FIG. 9A shows a front view of the device in FIG. 1 without nasal dilators for use as a mandibular repositioner.
Figure 9B:
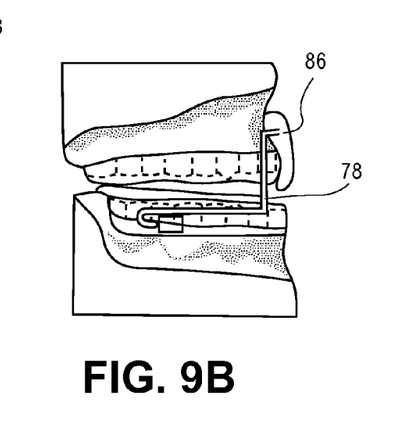
FIG. 9B shows the mandibular repositioner of FIG. 9A in its functional position shown on upper and lower dental models.

FIGS. 9A-9B—Additional Embodiments

Additional embodiments are shown in FIGS. 9A and 9B; FIG. 9A shows the front view of the device for mandibular reposition which has uses for orthodontic care. FIG. 9B shows device in place repositioning the mandible forward. This embodiment functions as a mandibular repositioning device which can be used for snoring and sleep apnea therapy or in orthodontics as the device to reposition the mandible and stimulate the growth of the mandible in orthodontic treatment. It differs from the preferred embodiment utilizes the device without nasal dilator apparatus 87.

FIGS. 10A-10E—Alternative Embodiments

Figure 10A:
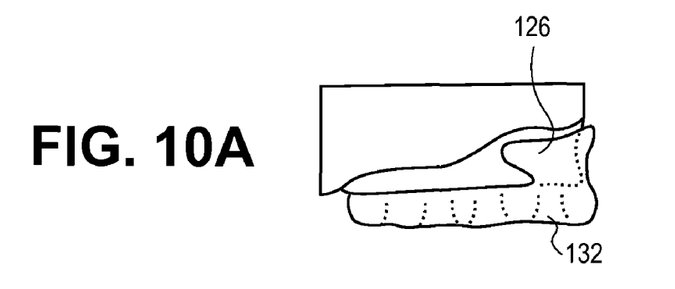
FIGS. 10A-10C show several alternative embodiments for athletic mouth guards.
Figure 10B:
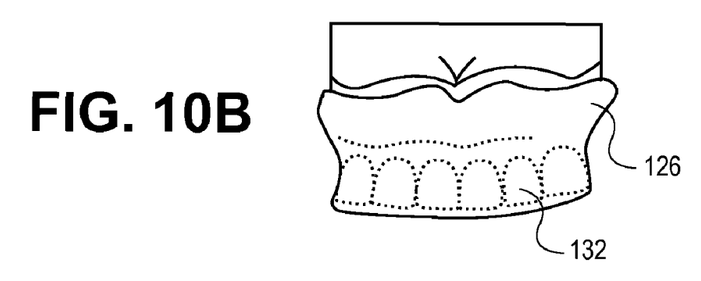

FIGS. 10A and 10B. show frontal and lateral views of an athletic mouth guard 132 which is constructed of molded commercially available materials shaped to extend up into the space between the upper jaw and the upper lip and stretch the nasal-labial soft tissue to function as a nasal dilator.

Figure 10C:
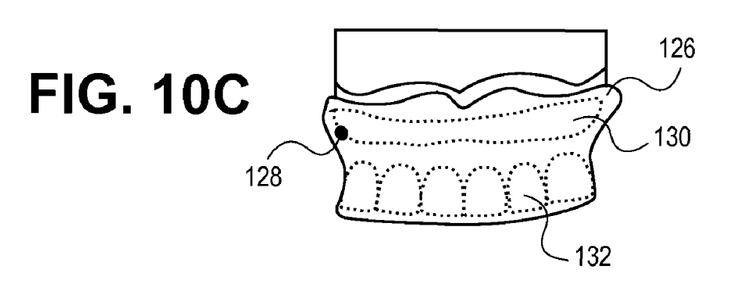

FIG. 10C shows an additional alternative embodiment of an athletic mouth guard 132 of similar form to that of FIGS. 10A and 10B. This contains a chamber in the flange 126 which extends into the space under the upper lip. This space can be filled with substance which allows control of the pressure in the chamber. This chamber 130 can be pressurized by substances such as liquid or air and allows adjustment of the volume of the flange 126 thereby adjusting the control of effect of tissue stretch and also providing a cushioning and protecting effect of the mouth guard 130.

Figure 10D:
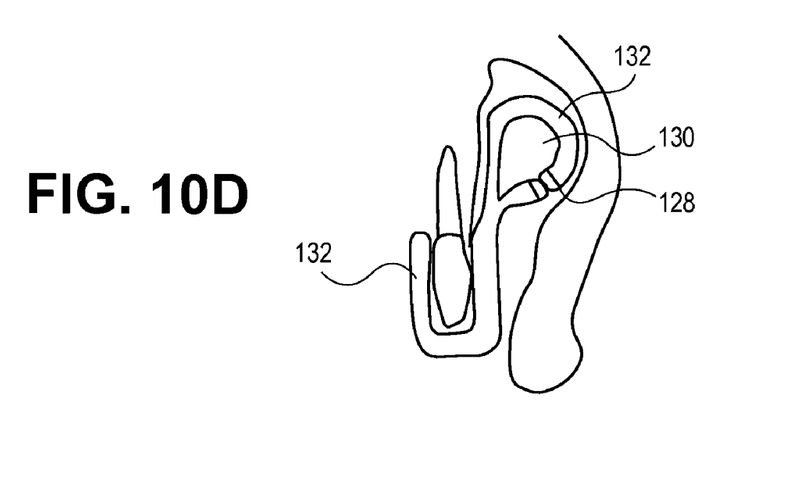
FIG. 10D shows a cross-sectional cut view of fluid or air chamber.

FIG. 10D shows a cross-section through the device in FIG. 10C. The device fits over the teeth as a mouth guard 132 and extends between the upper jaw and the upper lip. This cross-section shows the chamber 130 with a valve 128 in which an injection syringe (not shown) can be used to pressurize the chamber 130.

Figure 10E:
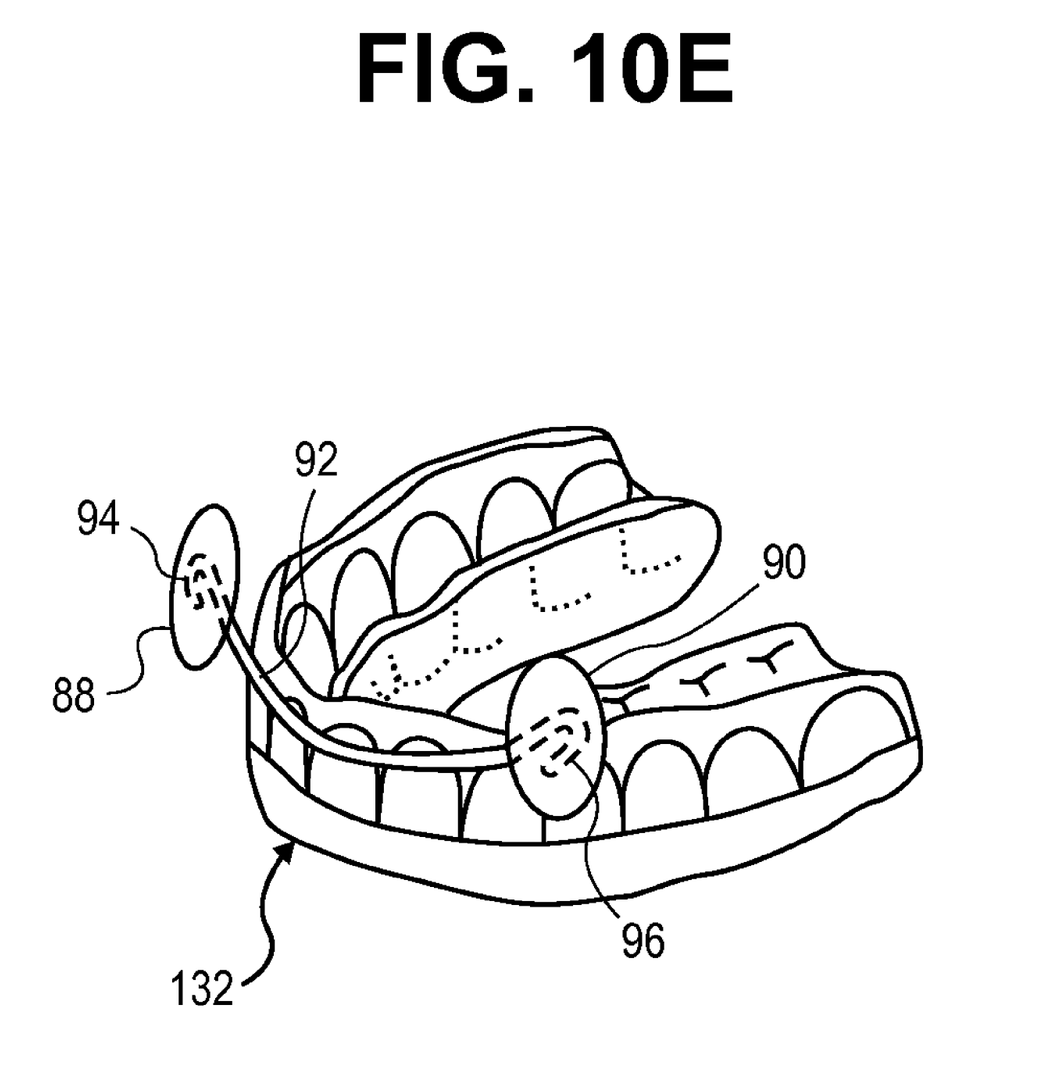
FIG. 10E shows an athletic mouth guard with nasal labial dilator buttons

FIG. 10E shows an additional embodiment. Nasal dilator apparatus 87 is attached to a mouth guard which can be used in non-contact activities.

CONCLUSION, RAMIFICATIONS, AND SCOPE

Thus the reader will see that this device creates improved airflow through the nasal and pharyngeal regions. It is used at night during sleep in the treatment of snoring and sleep apnea, which are medical conditions which carry significant medical morbidity and mortality. It can also be used to enhance breathing in times of needed maximal nasal pharyngeal respiration during waking activities such as during athletic activities.

Resistance to air flow through the nasal and posterior pharyngeal airway lead to snoring and sleep apnea. This health condition has a significant impact on millions of people. This device functions to prevent the closure of the breathing passageways in both the nose and throat regions.

These goals are accomplished because the device maintains maximum intraoral volume and eliminates the need for components which extend through the lips, outside of the mouth. It provides adjustability and significant degree of motion, which reduces strain on the dentition.

The advantages of this appliance are the synergistic effect of maintaining the airway in two different areas of resistance at the same time with one device. It accomplishes this with a device that is easy to use, has a minimal of material interfering with the tongue, has no components which extend out through lips, and which minimizes discomfort and forces on the teeth.

While my above description contains many specificities, they should not be construed as limitations to the scope of the invention, but rather as an exemplification of one preferred embodiment. Many other variations are possible. For example the nasal dilator apparatus can be constructed in a way so that it can be incorporated into sports mouth guards which can function both as a means maintaining maximum airflow through the nose while providing a cushion to protect the face during contact sport. This embodiment can use chambers, which contain air or liquid, which create a volume of material under the upper lip in the vestibule, which stretch as the nasal labial tissue and provides a cushion for impacts on the facial region.

The apparatus can also consist of molded acrylic material, plastics, or molded material forming a chamber, which contains air under pressure or water that creates hydraulic pressure. The pressure of this chamber can be constructed to allow adjustability of the size and pressure of the nasal dilator apparatus by means of a valve, which allows addition or subtraction of air or liquid.

Other uses of this device are for treatment of mouth breathers, who have developed a short upper lip. The device can be used to stretch the upper lip. The device can also be used in orthodontics as a lower jaw repositioner to correct malocclusions.

Accordingly, the scope of the invention should be determined, not by the embodiments illustrated, but by the appended claims and their legal equivalents.

The invention claimed is:

1. A mouth guard adapted to be seated at least partially on an upper jaw of a user to reduce resistance of air flow in a nasal channel of the user, comprising:

a lateral wall;

a lingual wall; and an occlusal wall connecting the lateral wall and the lingual wall so that when the mouth guard is seated at least partially on the upper jaw, the mouth guard is adapted to be held in place by contact of the lateral wall and the lingual wall with teeth of the upper jaw; and a flange extends extending from the lateral wall and adapted to be positioned between the upper jaw and an associated upper lip such that the flange extends above a gum line of the upper jaw and urges the upper lip away from the upper jaw, thereby dilating the nasal channel to reduce resistance of air flow in the nasal channel; and a chamber within the flange having an adjustable volume so that the upper lip is selectively urged away from the upper jaw when the mouth guard is seated at least partially on the upper jaw;

wherein the mouth guard is shaped to fit securely over a portion of the upper jaw.

2. A mouth guard adapted to be seated at least partially on an upper jaw of a user to reduce resistance of air flow in a nasal channel of the user, comprising:

a flange adapted to be positioned between the upper jaw and an associated upper lip such that the flange extends above a gum line of the upper jaw; and a chamber within the flange including a valve to adjust the volume of the chamber so that when the mouth guard is seated at least partially on the upper jaw a pressure applied by the flange to the upper lip is adjustable to affect dilation of the nasal channel resulting from such pressure, thereby allowing the user to selectively reduce resistance of air flow in the nasal channel;

wherein the mouth guard is formed by molding a thermoplastic material; and wherein the mouth guard is molded from a cast of the upper jaw.

3. A device adapted to be positioned at least partially in a mouth of a user to reduce resistance of air flow in a nasal channel, comprising:

a mouth guard adapted to be removably mounted on an upper jaw of the mouth, a nasal dilator extending from the mouth guard so that when the mouth guard is removably mounted on the upper jaw, the nasal dilator is adapted to extend above a gum line of the upper jaw; and wherein when the mouth guard is removably mounted on the upper jaw, the nasal dilator is adapted to apply pressure to the upper lip, thereby dilating the nasal channel; and wherein the nasal dilator is a pair of nasio-labial dilator buttons adjustably connected with the mouth guard by one or more button wires.

* * * * *